(12) United States Patent
Goss et al.

(10) Patent No.: US 6,341,522 B1
(45) Date of Patent: Jan. 29, 2002

(54) WATER WEIGHT SENSOR ARRAY IMBEDDED IN A SHEETMAKING MACHINE ROLL

(75) Inventors: John D. Goss, San Jose; Lee Chase, Los Gatos, both of CA (US)

(73) Assignee: Measurex Corporation, Cupertino, CA (US)

( * ) Notice: Subject to any disclaimer, the term of this patent is extended or adjusted under 35 U.S.C. 154(b) by 0 days.

(21) Appl. No.: 09/056,932

(22) Filed: Apr. 6, 1998

Related U.S. Application Data

(63) Continuation-in-part of application No. 08/766,864, filed on Dec. 13, 1996, now Pat. No. 5,891,306.

(51) Int. Cl.[7] .............................................. G01L 5/04
(52) U.S. Cl. ................................................. 73/159; 73/73
(58) Field of Search ............................. 73/159, 73, 74, 73/745, 160; 162/198

(56) References Cited

U.S. PATENT DOCUMENTS

| | | | |
|---|---|---|---|
| 3,206,642 A | 9/1965 | Canter et al. ................... 361/7 |
| 3,246,216 A | * 4/1966 | Mead et al. .................... 73/73 |
| 3,593,128 A | 7/1971 | Perry ........................... 324/61 |
| 3,622,448 A | * 11/1971 | Adams et al. ............... 162/198 |
| 3,630,836 A | 12/1971 | Bietry et al. ................ 162/198 |
| 3,636,327 A | 1/1972 | Troutman .................. 702/175 |
| 3,646,434 A | 2/1972 | Norwich ..................... 324/669 |
| 3,654,075 A | 4/1972 | Keyes et al. ................ 162/254 |
| 3,713,966 A | 1/1973 | Lippke ........................ 162/263 |
| 3,723,865 A | 3/1973 | Batey et al. ................ 328/612 |
| 3,795,984 A | 3/1974 | Meyer ........................... 34/46 |
| 3,811,087 A | 5/1974 | Schmelzer ................. 324/58.5 |
| 3,823,371 A | * 7/1974 | Lippke ....................... 162/263 |
| 3,864,626 A | 2/1975 | MacLean et al. ......... 324/61 R |
| 3,879,660 A | * 4/1975 | Piso ............................. 73/160 |
| 3,986,110 A | 10/1976 | Overall et al. ............ 324/61 R |
| 4,051,719 A | * 10/1977 | Loch .............................. 73/73 |
| 4,055,077 A | * 10/1977 | Loch .............................. 73/73 |
| 4,135,151 A | 1/1979 | Rogers ...................... 324/61 R |
| 4,259,632 A | 3/1981 | Ahtiainen ................. 324/61 R |
| 4,314,878 A | 2/1982 | Lee ............................. 162/198 |
| 4,329,201 A | 5/1982 | Bolton ........................ 162/198 |
| 4,369,080 A | 1/1983 | Johnson ........................ 156/64 |
| 4,398,996 A | 8/1983 | Bolton et al. ................ 162/198 |
| 4,468,611 A | 8/1984 | Tward ....................... 324/61 R |
| 4,474,643 A | 10/1984 | Lindblad ..................... 162/198 |
| 4,514,812 A | 4/1985 | Miller et al. ................. 364/473 |
| 4,580,233 A | 4/1986 | Parker et al. ............... 364/550 |
| 4,588,943 A | 5/1986 | Hirth .......................... 324/618 |
| 4,613,406 A | 9/1986 | Gess ............................ 162/49 |
| 4,680,089 A | 7/1987 | Aral et al. .................. 162/198 |
| 4,682,105 A | * 7/1987 | Thorn .......................... 73/159 |
| 4,692,616 A | 9/1987 | Hegland et al. .......... 250/252.1 |
| 4,707,779 A | 11/1987 | Hu .............................. 364/148 |
| 4,748,400 A | 5/1988 | Typpo ....................... 324/61 R |

(List continued on next page.)

*Primary Examiner*—Hezron Williams
*Assistant Examiner*—Michael Cygan
(74) *Attorney, Agent, or Firm*—Burns Doane Swecker & Mathis; Anthony Miologos

(57) ABSTRACT

A sensor imbedded roller for detecting changes in properties of a material and a measurement apparatus including a fixed impedance element coupled in series with a variable impedance sensor imbedded roller between an input signal and a reference potential (e.g. ground) is described. The sensor, which includes an electrode configuration, is imbedded into a roller such that when it rotates it comes in contact with the material being measured and its impedance varies. The variable impedance of the sensor relates to changes in property of the material being sensed which can then be related to changes in other physical characteristics of the material such as weight, chemical composition, and temperature. Sensor imbedded rollers can be placed in a sheet-making machine to measure the pre-formed and post-formed paper product.

19 Claims, 8 Drawing Sheets

U.S. PATENT DOCUMENTS

| | | | |
|---|---|---|---|
| 4,786,529 A | 11/1988 | Boissevain | 427/296 |
| 4,791,353 A | 12/1988 | Typpo | 324/61 R |
| 4,817,021 A | 3/1989 | Sowerby et al. | 364/558 |
| 4,827,121 A | 5/1989 | Vidrine, Jr. et al. | 250/227 |
| 4,840,706 A | 6/1989 | Campbell | 162/198 |
| 4,845,421 A | 7/1989 | Howarth et al. | 324/61 R |
| 4,903,528 A | 2/1990 | Balakrishnan et al. | 73/159 |
| 4,909,070 A | 3/1990 | Smith | 73/73 |
| 4,921,574 A | 5/1990 | Hu | 162/198 |
| 4,924,172 A | 5/1990 | Homgren | 324/664 |
| 4,947,684 A | 8/1990 | Balakrishnan | 73/159 |
| 4,957,770 A | 9/1990 | Howarth | 427/9 |
| 4,980,846 A | 12/1990 | Chapman | 700/167 |
| 4,986,410 A | 1/1991 | Shields | 198/444 |
| 4,990,261 A | 2/1991 | Ho | 210/709 |
| 4,994,145 A | 2/1991 | Seymour | 162/49 |
| 5,013,403 A | 5/1991 | Chase | 162/49 |
| 5,020,469 A | 6/1991 | Boissevain et al. | 118/67 |
| 5,021,740 A | 6/1991 | Sarr et al. | 324/687 |
| 5,022,966 A | 6/1991 | Hu | 162/198 |
| 5,045,798 A | 9/1991 | Hendrick | 324/687 |
| 5,052,223 A | 10/1991 | Regnault et al. | 73/304 C |
| 5,067,345 A | 11/1991 | Mougne | 73/61.1 R |
| 5,093,795 A | 3/1992 | Lewis | 700/129 |
| 5,122,754 A | 6/1992 | Gotaas | 324/676 |
| 5,124,552 A | 6/1992 | Anderson | 250/339 |
| 5,132,631 A | 7/1992 | Klopfenstein et al. | 324/676 |
| 5,134,380 A | 7/1992 | Jonas | 324/674 |
| 5,170,128 A | 12/1992 | Masurat et al. | 324/664 |
| 5,170,670 A | 12/1992 | Fasching et al. | 73/861.08 |
| 5,177,445 A | 1/1993 | Cross | 324/637 |
| 5,198,777 A | 3/1993 | Masuda et al. | 324/671 |
| 5,206,599 A | 4/1993 | Mayer | 324/671 |
| 5,208,544 A | 5/1993 | McBrearty et al. | 324/687 |
| 5,212,452 A * | 5/1993 | Mayer et al. | 324/662 |
| 5,225,785 A | 7/1993 | Mayer et al. | 324/671 |
| 5,241,280 A * | 8/1993 | Aidun et al. | 324/671 |
| 5,247,261 A * | 9/1993 | Gershenfeld | 324/716 |
| 5,262,955 A * | 11/1993 | Lewis | 700/129 |
| 5,270,664 A * | 12/1993 | McMurtry et al. | 324/690 |
| 5,340,442 A * | 8/1994 | Gess et al. | 162/198 |
| 5,400,247 A * | 3/1995 | He | 700/53 |
| 5,450,015 A * | 9/1995 | Mastico et al. | 324/665 |
| 5,492,601 A * | 2/1996 | Ostermayer et al. | 162/198 |
| 5,493,910 A * | 2/1996 | Hall et al. | 700/597 |
| 5,539,634 A * | 7/1996 | He | 700/38 |
| 5,561,599 A * | 10/1996 | Lu | 700/44 |
| 5,563,809 A * | 10/1996 | Williams et al. | 364/560 |
| 5,636,126 A * | 6/1997 | Heaven et al. | 700/129 |
| 5,658,432 A * | 8/1997 | Heaven et al. | 162/198 |

* cited by examiner

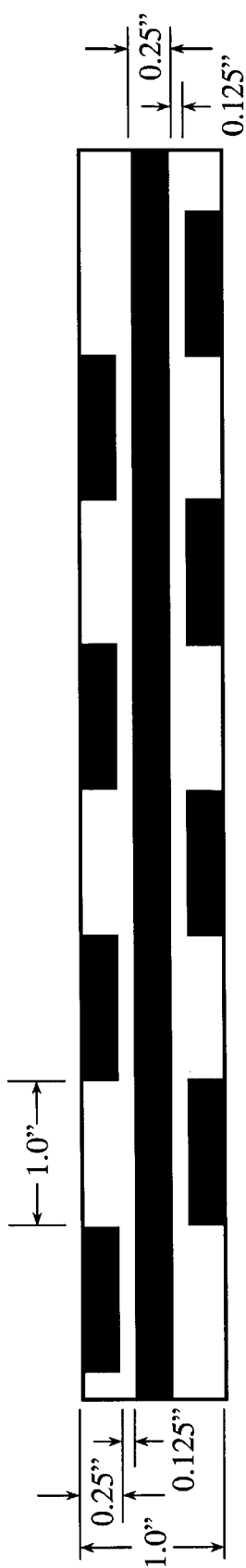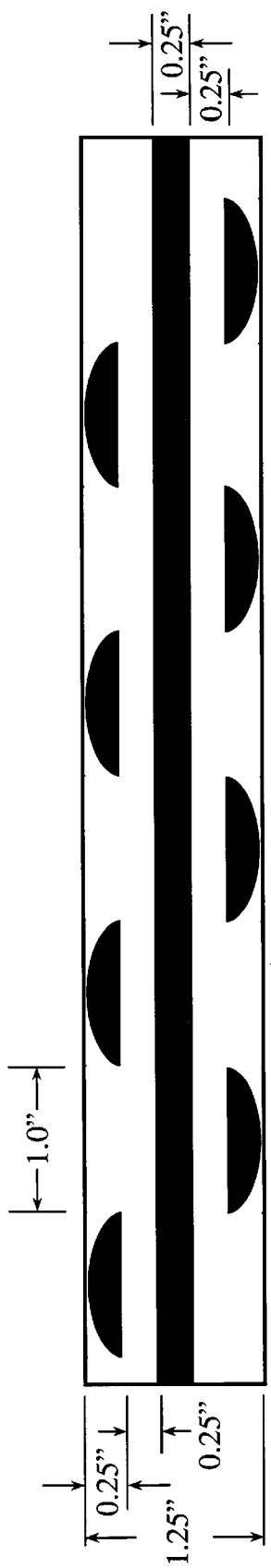
Fig. 7
Fig. 8

WATER WEIGHT SENSOR ARRAY IMBEDDED IN A SHEETMAKING MACHINE ROLL

CROSS REFERENCE TO RELATED APPLICATIONS

This is a continuation-in-part of U.S. Patent application No. 08/766,864 filed Dec. 13, 1996, now U.S. Pat. No. 5,891,306 assigned to the assignee of the present application.

BACKGROUND OF THE INVENTION

1. Field of the Invention

The present invention generally relates to systems for controlling continuous sheetmaking systems and, more specifically, to sensors for measuring the fiber weight of wetstock in a papermaking machine.

2. State of the Art

In the art of modern high-speed papermaking, it is well known to continuously measure certain properties of the paper material in order to monitor the quality of the finished product. These on-line measurements often include basis weight, moisture content, and sheet caliper (i.e., thickness). The measurements can be used for controlling process variables with the goal of maintaining output quality and minimizing the quantity of product that must be rejected due to upsets in the manufacturing process.

The on-line sheet property measurements are often accomplished by scanning sensors that periodically traverse the sheet material from edge to edge. For example, a high-speed scanning sensor may complete a scan in a period as short as twenty seconds, with measurements being read from the sensor at about 50 milliseconds intervals. It is also know that a series of stationary sensors can be used to make similar on-line measurements.

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers complete the drying process. The paper machine is, in essence, a de-watering, i.e., water removal, system. A typical forming section of a papermaking machine includes an endless traveling papermaking mesh fabric or wire which travels over a series of water removal elements such as table rolls, foils, vacuum foils, and suction boxes. As the material travels on the mesh fabric over the series of water removal elements, there is a distinct line of demarcation showing a change in the state of the stock from an extremely wet state to a relatively dryer state. This visible line of demarcation (referred to as the dry line) is characterized in that one side of the dry line has a glossy appearance (i.e., wet state) and the other side of the line has a non-glossy appearance (i.e., relatively dry state). The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Other, papermaking devices well known in the art are described for example in U.S. Pat. No. 5,400,258.

Many factors influence the rate at which water is removed which ultimately affects the quality of the paper produced. As is apparent, it would be advantageous to monitor the dynamic process so as to, among other things, predict and control the dry stock weight of the paper that is produced.

It is conventional to measure the moisture content on leaving the main dryer section or at the take up reel employing scanning sensors. Such measurement may be used to adjust the machine operation toward achieving desired parameters. One technique for measuring moisture content is to utilize the absorption spectrum of water in the infra-red. Monitoring or gauge apparatus for this purpose is commonly in use. Such apparatus conventionally uses either a fixed gauge or a gauge mounted on a scanning head which is repetitively scanned transversely across the web at the exit from the dryer section and/or upon entry to the take up reel, as required by the individual machines. The gauges typically use a broad-band infra-red source and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web.

SUMMARY OF THE INVENTION

The present invention, in general, is a sensor imbedded roller which, in one embodiment, is used in a measurement apparatus in a sheetmaking machine. In a preferred embodiment, the measurement apparatus includes a fixed impedance element coupled in series with a detection cell in the sensor which is coupled between an input signal and a reference potential (e.g., ground) and which has a variable impedance. The fixed impedance element and the detection cell form a voltage divider network such that changes in impedance of the detection cell results in changes in voltage on the output of the measurement system. The impedance of the detection cell represents the impedance of the physical configuration of electrodes within the sensor and the material residing between and in close proximity to the electrodes. The impedance relates to the property of the material being measured.

In one embodiment, the measurement apparatus is used to measure the conductivity of an aqueous mixture (referred to as wetstock) in a sheetmaking system. The conductivity of the wetstock is directly proportional to the total water weight within the wetstock, consequently providing information which can be used to monitor and control the quality of the paper sheet produced by the papermaking system. In this embodiment the sensor imbedded roller is positioned in the wet end of the sheetmaking system so as to detect conductivity changes.

In another embodiment, the measurement apparatus is used to measure the weight of dry paper sheet in a sheetmaking machine. In this application, the conductivity is negligible and the capacitive impedance is inversely proportional to the dielectric constant and the amount of paper between the electrodes of the measurement apparatus. In this embodiment the sensor embedded roller is positioned in the dry end of the sheetmaking system so as to detect capacitive impedance changes.

The fixed impedance element can be embodied as a resistor, capacitor, inductor or a combination of the three and the input signal is an analog signal. In the embodiment in which the impedance element is an inductor, the impedance of the inductor can be selected to be a particular magnitude by setting the frequency of the input signal so that the impedance of the fixed impedance element can be set to the same range as the impedance of the sensor for optimum sensor sensitivity. Hence, in the case in which the impedance of the sensor varies due to fluctuations in operating conditions of the system or the material being sensed, the impedance of the inductor can be customized to match the sensor impedance without any hardware changes.

The sensor comprises an array of electrodes having a particular configuration which forms measurement cells, each cell being independently coupled to an input signal provided by a signal generator through the impedance element. In a preferred embodiment used to detect the conductivity of an aqueous fibrous mixture, the impedance elements are implemented as resistive elements. Each cell forms a voltage divider network made-up of the resistive element coupled between the signal generator and portions or segments of electrodes within a given cell and of a resistance resulting from the effective water resistance between the electrode portions and segments. The output of each cell is taken from an electrode segment or portion, i.e., the point between the resistive element and the cell. As the conductance of the aqueous mixture changes so does the output voltage of the cell. The output voltage of each cell is coupled to a detector which, in one embodiment, includes circuitry for enhancing the signal such as an amplifier for amplifying the output signal from each cell and a rectifier. In one embodiment of the present invention the detector includes circuitry for converting the output voltages from each cell into data relating to the weight of the aqueous mixture or to other aqueous mixture characteristics.

A first embodiment of the sensor electrode configuration includes first and second elongated segmented side electrodes and a center elongated electrode spaced-apart and centered between the side electrodes all in essentially the same plane. Segments in the two side electrodes are configured such that the segments in the first segmented electrode are staggered with respect to segments in the second segmented electrode. A cell within the first embodiment array configuration is defined as including one of the segments and a corresponding portion of the center electrode opposite to that segment. In a second embodiment, the first embodiment sensor array includes additional grounded electrodes situated along side each of the first and second segmented electrodes so as to guard against current leakage to conductors in the vicinity of the electrodes.

A third embodiment of the sensor electrode configuration includes two elongated grounded side electrodes and a center segmented elongated electrode spaced-apart and centered between the side electrodes. A cell within the third embodiment electrode configuration is defined as including one of the electrode segments in the center electrode and the corresponding portion of the grounded side electrodes situated adjacent to and opposite of this center electrode segment. The fourth embodiment of the electrode configuration is a variation of the third electrode configuration in that it includes a single grounded elongated electrode adjacent a single elongated segmented electrode.

In a preferred embodiment, the apparatus includes a feedback circuit which is used to adjust the input signal provided from the signal generator to compensate for changes in properties of the material that is not being sensed, but that also may affect the output voltages of the cells.

In a preferred embodiment, the measurement apparatus is used in a sheetmaking system which includes a web and at least one sensor electrode configuration imbedded into a roller in a sheetmaking system. As the roller turns, one of the electrode arrays comes in contact with the pre-formed paper material. When in contact, the array provides a read out giving an instantaneous cross-directional (CD) measurement. The sensor imbedded rollers can be mounted anywhere down the machine including the reel location. In one embodiment, the roller is positioned beneath the web and is driven at the same speed as the web such that the point of contact of an electrode array and the web does not move thereby eliminating sliding friction, wear on the array, and residue build-up on the array.

In another embodiment, more than one (CD) electrode array is imbedded in the circumference of the roll so as to provide more than one CD measurement as the roll rotates and each of the imbedded arrays come in contact with the web. In still another embodiment, four CD arrays are imbedded in the roll such that four measurements are provided for each revolution of the roll.

In one embodiment, the sensor imbedded roller includes a stationary center portion covered by a rotatable shell disposed about the center portion. At least one sensor is imbedded into the outer surface of the rotatable shell. The imbedded sensor on the outer surface of the rotatable shell is electrically connected to electrical contacts on the inner surface of the shell. Wires from the remainder of a measurement apparatus for coupling to the imbedded sensor are coupled to a sliding contact assembly attached to the stationary core portion. Electrical contact is made with outer surface imbedded sensors as the inner surface contacts of the rotatable shell pass over the sliding contact assembly. Each sensor in the shell uses the same sliding contact assembly such that only one is in contact with it at a time so as to detect property changes of the material being sensed.

In another embodiment, the sensor imbedded roller includes processing circuitry, and in one embodiment, the processing circuitry serializes measurement data received from the sensor to minimize the number of external wire connections coming from the roller.

In a preferred embodiment, the sensor embedded roller is implemented with a metal surface or a metal roll imbedded with dielectric insulating layers and metal layers to form the electrode array. In one particular embodiment, the metal is steel.

In still another embodiment, the paper sheet is rolled around the roller so as to prolong sensor and material contact to provide an extended measurement time.

BRIEF DESCRIPTION OF THE DRAWINGS

FIGS. 4–9 show various embodiments of the sensor array electrode configurations;

DESCRIPTION OF THE PREFERRED EMBODIMENTS

The present invention is a measurement apparatus including a sensor imbedded roller for measuring properties of material and, in one embodiment, for determining the weight of sheetmaking materials in a sheet making system. In the following description, numerous specific details are set forth, such as particular uses of the system, resistive values, frequencies, etc. In order to provide a thorough understanding of the present invention. It will be obvious, however, to one skilled in the art that these specific details need not be employed to practice the present invention. In other instances, well understood sheetmaker system structures have not been described in detail in order to avoid unnecessarily obscuring the present invention.

Figure 1:
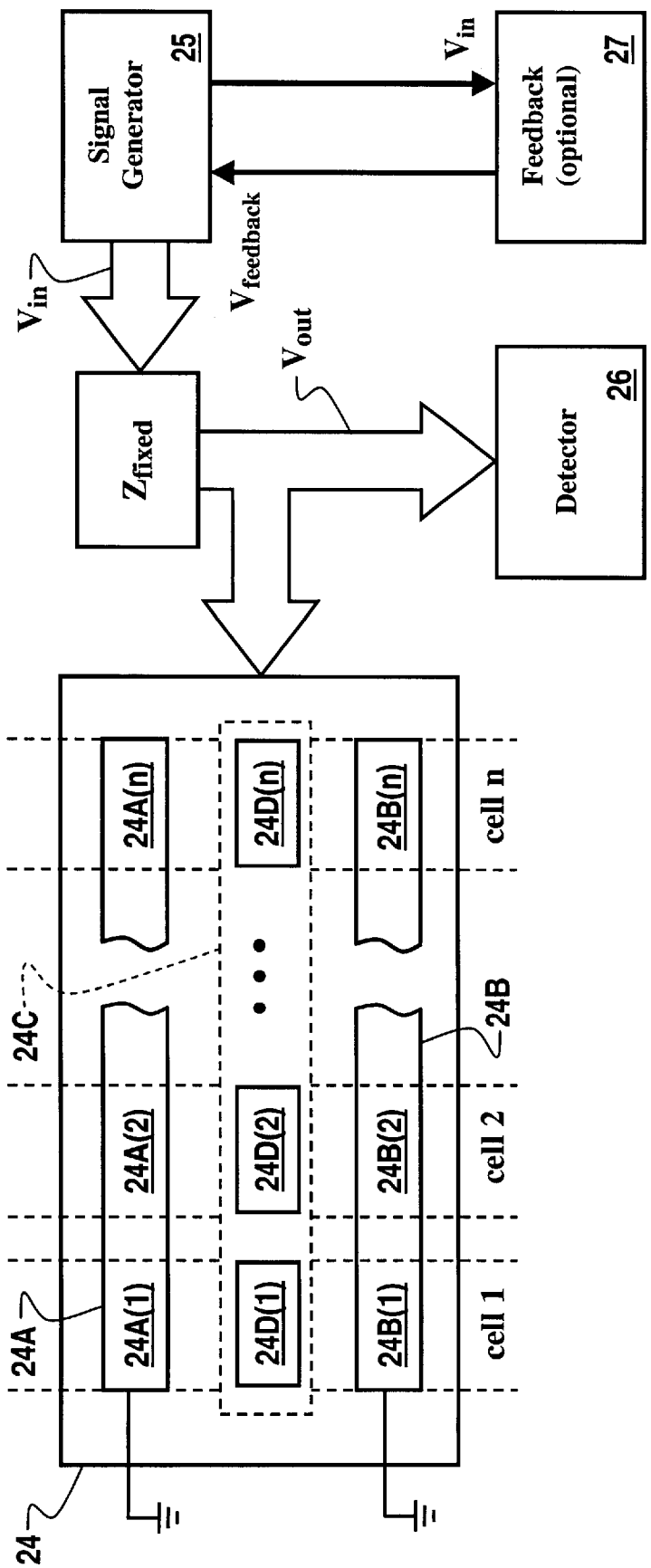
FIG. 1 shows a block diagram of a measurement apparatus having a first sensor array configuration.

FIG. 1 shows a moisture measurement system, described in U.S. Pat. No. 5,891,306 assigned to the assignee of the present application which in one embodiment measures the conductivity of the water in the stock material using a sensor array having a first configuration. The conductivity of the water is proportional to the water weight. The sensor array includes two elongated grounded electrodes 24A and 24B and a segmented electrode 24C. Measurement cells (cell1, cell2, ... celln) each include a segment of electrode 24C and a corresponding portion of the grounded electrodes (24A and 24B) opposite the segment. Each cell detects the conductivity of the paper stock and specifically the water portion of the stock residing in the space between the segment and its corresponding opposing portions of grounded electrode.

Each cell is independently coupled to an input voltage (Vin) from signal generator 25 through an impedance element Zfixed and each provides an output voltage to voltage detector 26 on bus Vout. Signal generator 25 provides Vin. In one embodiment Vin is an analog waveform signal, however other signal types may be used such as a DC signal. In the embodiment in which signal generator 25 provides a waveform signal it may be implemented in a variety of ways and typically includes a crystal oscillator for generating a sinewave signal and a phase lock loop for signal stability. One advantage to using an AC signal as opposed to a DC signal is that it may be AC coupled to eliminate DC off-set.

Detector 26 includes circuitry for detecting variations in voltage from each of the segments in electrodes 24C and any conversion circuitry for converting the voltage variations into useful information relating to the physical characteristics of the aqueous mixture. Optional feedback circuit 27 includes a reference cell having similarly configured electrodes as a single cell within the sensor array. The reference cell functions to respond to unwanted physical characteristic changes in the aqueous mixture other than the physical characteristic of the aqueous mixture that is desired to be measured by the array. For instance, if the sensor is detecting voltage changes due to changes in weight, the reference cell is configured so that the weight remains constant. Consequently, any voltage/conductivity changes exhibited by the reference cell are due to aqueous mixture physical characteristics other than weight changes (such as temperature and chemical composition). The feedback circuit uses the voltage changes generated by the reference cell to generate a feedback signal (Vfeedback) to compensate and adjust Vin for these unwanted aqueous mixture property changes (to be described in further detail below). It should also be noted that the non-weight related aqueous mixture conductivity information provided by the reference cell may also provide useful data in the sheetmaking process.

Figure 2A:
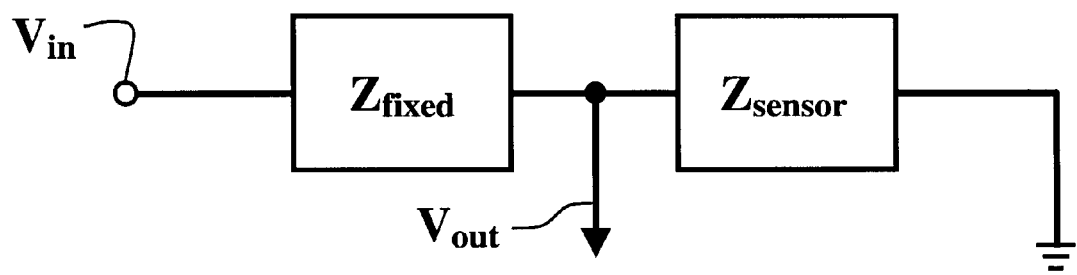
FIG. 2A shows a basic electrical diagram of a measurement apparatus using a sensor block having a variable impedance and 2B shows an equivalent circuit of the sensor block shown in FIG. 2A.
Figure 2B:
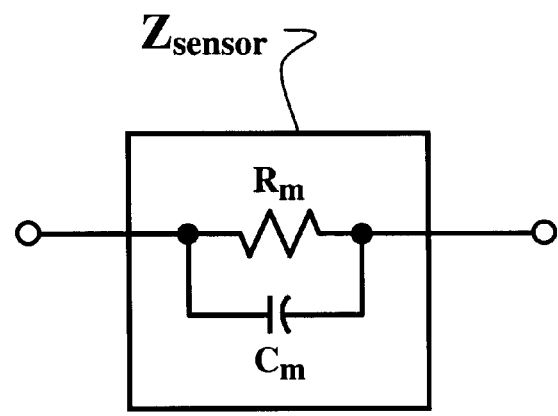

FIG. 2A is a block diagram illustrating the general concept of the measuring apparatus as described in U.S. Pat. No. 5,891,306. The measuring apparatus includes a fixed impedance element (Zfixed) coupled in series with a variable impedance block (Zsensor) between an input signal (Vin) and a reference potential (e.g., ground). The fixed impedance element may be embodied as a resistor, an inductor, a capacitor, or a combination of these elements. The fixed impedance element and the impedance of Zsensor form a voltage divider network such that changes in impedance of Zsensor results in changes in voltage on Vout. The impedance block Zsensor shown in FIG. 2A is representative of electrodes in the sensor array and the material residing between the electrodes. The impedance block, Zsensor, can also be represented by the equivalent circuit shown in FIG. 2B, where Rm is the resistance of the material between the electrodes and Cm is the capacitance of the material between the electrodes.

The sensor array is sensitive to three physical properties of the material being detected: the conductivity or resistance, the dielectric constant, and the proximity of the material to the sensor. Depending on the material, one or more of these properties will dominate. The material capacitance depends on the geometry of the electrodes, the dielectric constant of the material, and its proximity to the sensor. For a pure dielectric material, the resistance of the material is infinite (i.e., $Rm=\infty$) between the electrodes and the sensor measures the dielectric constant of the material. Alternatively, for a highly conductive material, the resistance of the material is much less than the capacitive impedance (i.e., $Rm<<Z_{Cm}$), and the sensor measures the conductivity of the material.

To measure material properties, Vin is coupled to the voltage divider network shown in FIG. 2A and changes in the variable impedance block (Zsensor) is measured on Vout. In this configuration the sensor impedance, Zsensor, is:

$$Zsensor=Zfixed*Vout/(Vin=Vout). \qquad \text{Eq. 1}$$

The changes in impedance of Zsensor relates to physical characteristics of the material such as material weight, temperature, and chemical composition. It should be noted that optimal sensor sensitivity is obtained when Zsensor is approximately the same as or in the range of Zfixed.

Figure 3:
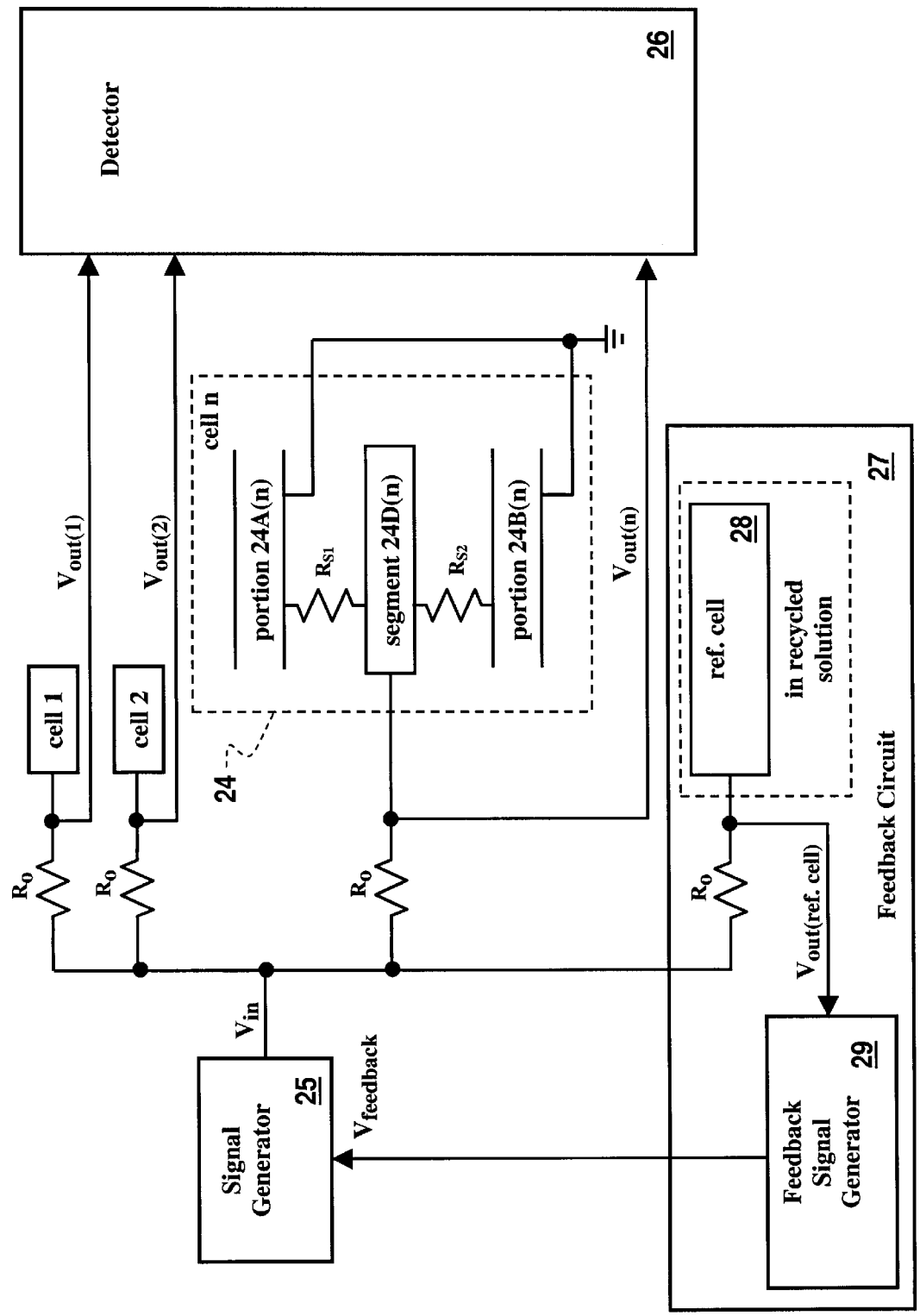
FIG. 3 shows an electrical representation of the measurement apparatus shown in FIG. 1.

FIG. 3 illustrates an electrical representation of a measuring apparatus including cells 1–n of sensor array 24 for measuring conductivity of an aqueous material. As shown, each cell is coupled to Vin from signal generator 25 through an impedance element which, in this embodiment, is resistive element Ro. Referring to cell n, resistor Ro is coupled to center segment 24D(n) and portions 24A(n) and 24B(n) (opposite segment 24D(n)) are coupled to ground. Also shown in FIG. 3 are resistors Rs1 and Rs2 which represent the conductance of the aqueous mixture between the segments and the grounded portions. Resistors Ro, Rs1, and Rs2 form a voltage divider network between Vin and ground.

The measuring apparatus shown in FIG. 3 is based on the concept that the conductivity of the voltage divider network Rs1 and Rs2 of the aqueous mixture and the weight/amount of an aqueous mixture are inversely proportional. Consequently, as the weight increases/decreases, the combination of Rs1 and Rs2 decreases/increases. Changes in Rs1 and Rs2 cause corresponding fluctuations in the voltage Vout as dictated by the voltage divider network. The voltage Vout from each cell is coupled to detector 26. Hence, variations in voltage inversely proportional to variations in conductivity of the aqueous mixture are detected by detector 26 thereby providing information relating to the weight and amount of aqueous mixture in the general proximity above each cell. Detector 26 may include means for amplifying the output signals from each cell and in the case of an analog signal will include a means for rectifying the signal to convert the analog signal into a DC signal. In one implementation well adapted for electrically noisy environments, the rectifier is a switched rectifier including a phase lock-loop controlled by Vin. As a result, the rectifier rejects any signal components other than those having the same frequency as the input signal and thus provides an extremely well filtered DC signal. Detector 26 also typically includes other circuitry for converting the output signals from the cell into information representing particular characteristics of the aqueous mixture.

FIG. 3 also shows feedback circuit 27 including reference cell 28 and feedback signal generator 29. The concept of the feedback circuit 27 is to isolate a reference cell such that it is affected by aqueous mixture physical characteristic changes other than the physical characteristic that is desired to be sensed by the system. For instance, if weight is desired to be sensed then the weight is kept constant so that any voltage changes generated by the reference cell are due to physical characteristics other than weight changes. In one embodiment, reference cell 28 is immersed in an aqueous mixture of recycled water which has the same chemical and temperature characteristics of the water in which sensor array 24 is immersed in. Hence, any chemical or temperature changes affecting conductivity experienced by array 24 is also sensed by reference cell 28. Furthermore, reference cell 28 is configured such that the weight of the water is held constant. As a result voltage changes Vout(ref cell) generated by the reference cell 28 are due to changes in the conductivity of the aqueous mixture, caused from characteristic changes other than weight. Feedback signal generator 29 converts the undesirable voltage changes produced from the reference cell into a feedback signal that either increases or decreases Vin and thereby cancels out the affect of erroneous voltage changes on the sensing system. For instance, if the conductivity of the aqueous mixture in the array increases due to a temperature increase, then Vout(ref. cell) will decrease causing a corresponding increase in the feedback signal. Increasing Vfeedback increases Vin which, in turn, compensates for the initial increase in conductivity of the aqueous mixture due to the temperature change. As a result, Vout from the cells only change when the weight of the aqueous mixture changes.

Figure 4:
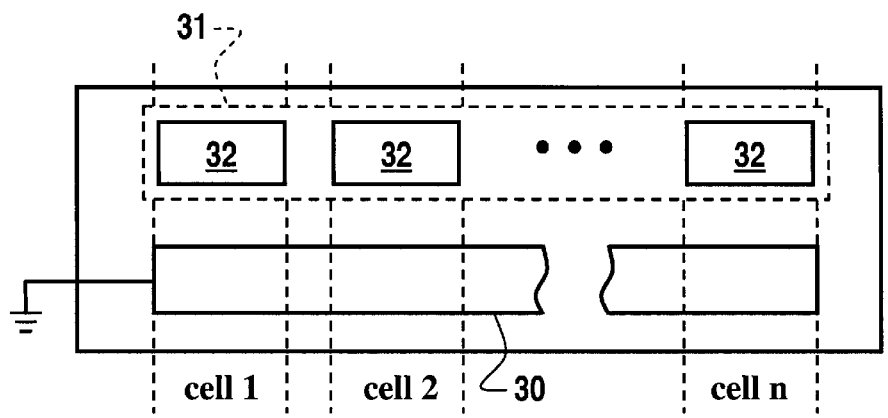

FIGS. 4–9 show various embodiments of sensor array electrode configurations. It should be understood that many variations are possible and that these are just an example of various possible embodiments of sensor arrays. FIG. 4 shows as electrode configuration which is a variation of the first electrode configuration shown in FIG. 1 and as disclosed in U.S. Pat. No. 5,891,306. This electrode configuration has a single grounded elongated electrode 30 and a segmented electrode 31 including a plurality of electrode segments 32. Each electrode configuration includes a plurality of measurement cells (cell 1, cell 2, . . . cell n) and each measurement cell includes an electrode segment 32 and a corresponding portion of the grounded elongated electrode 30.

Figure 5:
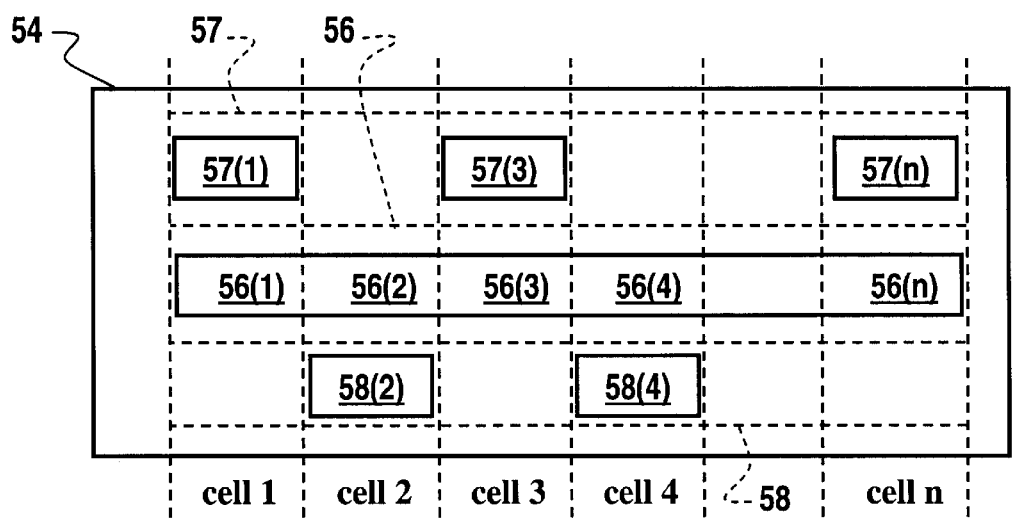

FIG. 5 shows a third embodiment of the electrode configuration as disclosed in a U.S. patent application Ser. No. 08/977,773 assigned to the assignee of the present application. This embodiment includes a first elongated electrode 56 coupled to a reference potential (e.g., ground) having electrode portions 56(1)–56(n) and elongated segmented electrodes 57 and 58 parallel to, in the same plane as, and on opposite sides, respectively, of electrode 56. Segmented electrode 57 is made-up of segments 57(1), 57(3) . . . 57(n) and segmented electrode 58 is made-up of segments 58(2), 58(4) . . . 58(n–1). The segments of electrodes 57 and 58 are configured with respect to each other such that segments in electrode 57 are staggered with respect to segments in electrode 58. A cell within array 54 is defined as including a segment from either of electrodes 57 or 58 and the portion of electrode 56 opposite that segment. For example, cell 1 includes segment 57(1) and portion 56(1).

Figure 6:
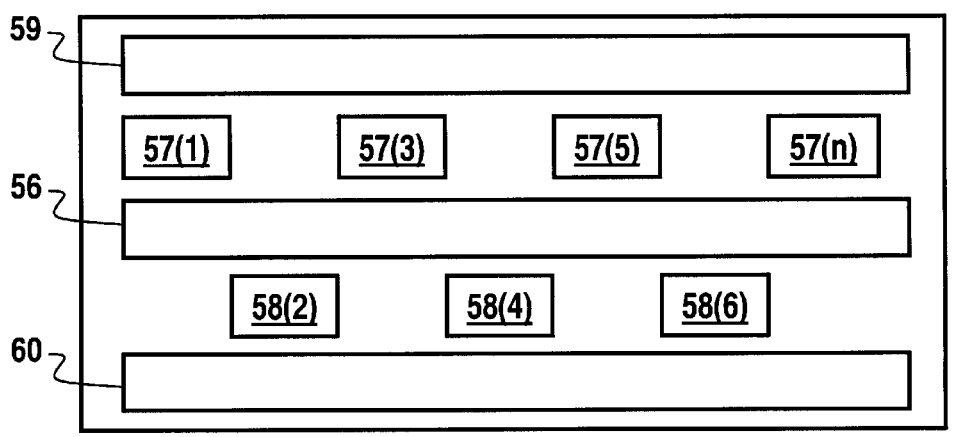

FIG. 6 shows an electrode configuration which is a variation of the sensor array configuration shown in FIG. 5 as disclosed in a U.S. patent application Ser. No. 08/977,773. This embodiment includes two additional grounded electrodes 59 and 60 on each side of electrodes 57 and 58 to eliminate the possibility of current leakage to nearby grounded conductors.

FIG. 7 shows another variation of the sensor array embodiment shown in FIG. 5 as disclosed in a U.S. patent application Ser. No. 08/977,773. In this embodiment, the total sensor array width is one inch. The spacing between a segment and its corresponding opposite electrode portion is 0.125 inch, which would be appropriate for thin water layer as found on fine paper machines. The width of the electrodes are 0.25 inch, thus providing an extremely compact sensor array.

FIG. 8 shows still another variation of the sensor array embodiment shown in FIG. 5 as disclosed in a U.S. patent application Ser. No. 08/977,773. In this embodiment, the sensor array has a width of 1.25 inches and has a wider spacing of 0.25 inch between a segment and its corresponding opposite electrode.

Figure 9:
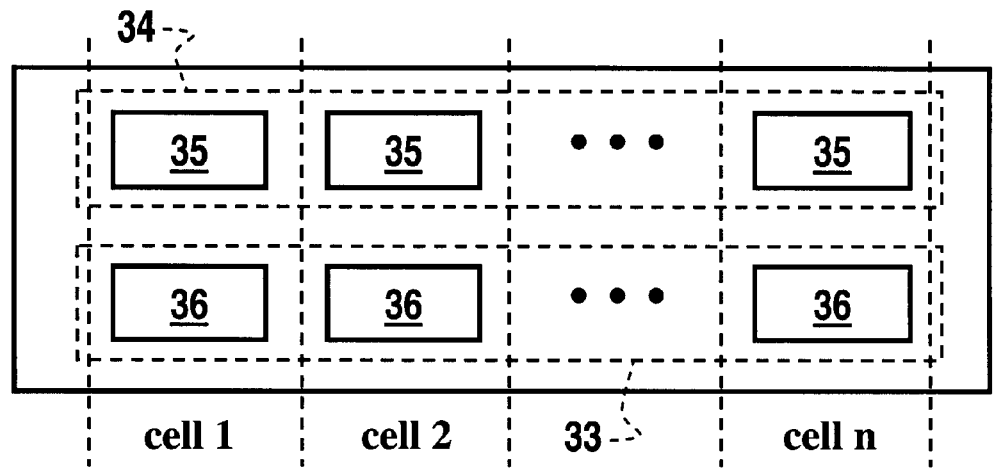

FIG. 9 shows a sensor array embodiment as disclosed in U.S. Pat. No. 5,891,306 which is particularly suited for sensing properties of material having extremely low conductivity (such as dry paper). In this case, the sensor measures the dielectric constant of the paper. As shown in FIG. 9, the electrode configuration includes two adjacent spaced-apart elongated segmented electrodes 33 and 34 each having electrode segments 36 and 35, respectively.

Figure 10:
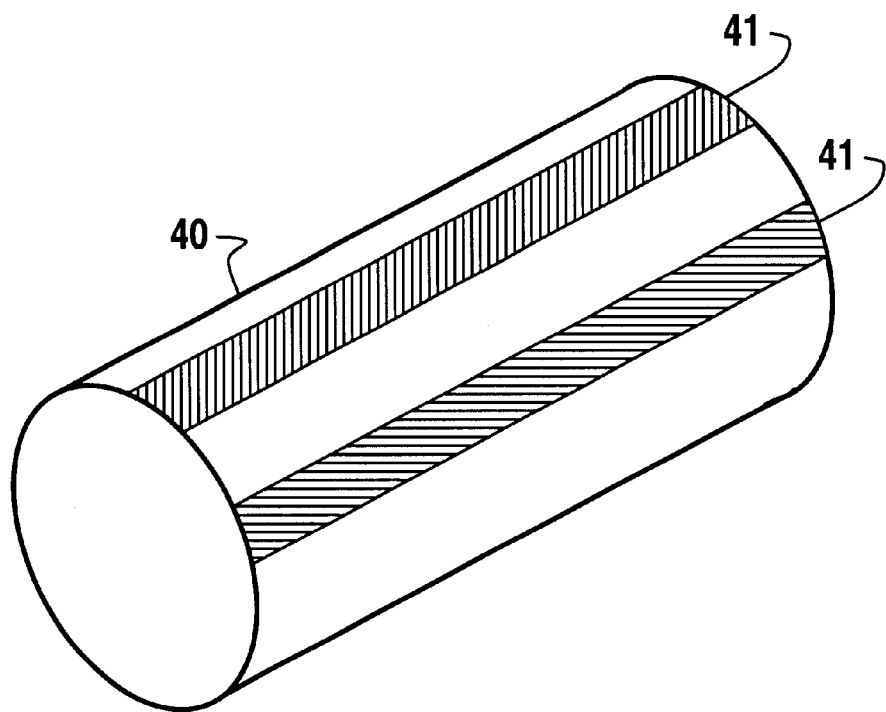
FIG. 10 shows a sensor imbedded roller in a sheetmaking machine roller in accordance with the present invention.

In general, the present invention is a rotatable roller having a sensor imbedded into it for detecting property changes of a material as it rotates and comes in contact with the material. The sensor has a variable impedance, such that changes in the impedance of the sensor corresponds to changes in the property of the material. FIG. 10 shows a sensor imbedded roller 40 which includes at least one sensor 41 (two are shown in FIG. 10) imbedded within the exterior side of roller 40. It should be understood that the sensor can include any electrode configuration as described above and that FIG. 10 does not show any particular configuration.

Figure 11:
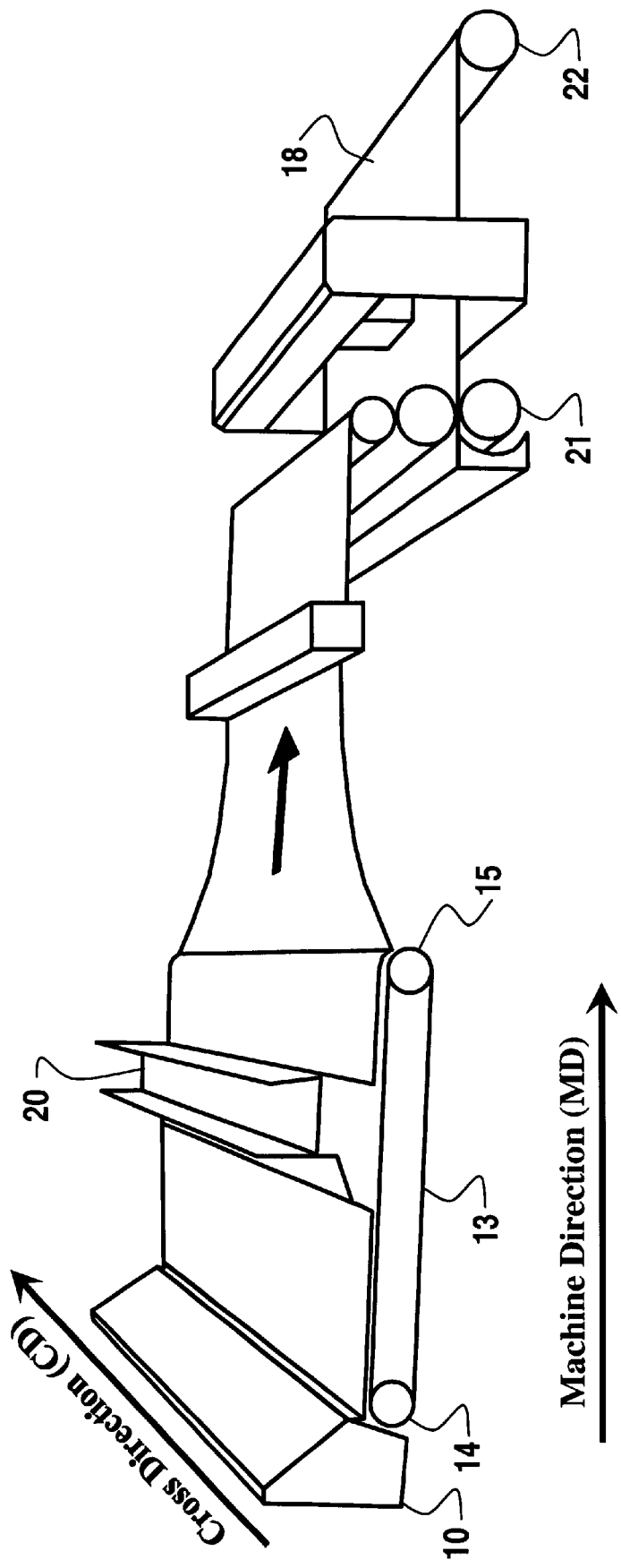
FIG. 11 shows a prior art sheetmaking machine for illustrating possible locations of sensor imbedded rollers.

In one particular embodiment, the sensor imbedded roller is for measuring physical characteristics of material in a sheetmaking machine. FIG. 11 shows a prior art typical sheetmaking system for producing a continuous sheet of paper material 18 including a headbox 10, a steambox 20, a calendaring stack 21, a take-up reel 22. In the headbox 10, actuators are arranged to control discharge of wetstock onto supporting web 13. The sheet 18 travels between rollers 14 and 15, and passes through a calendaring stack 21. The calendaring stack 21 includes actuators 24 that control the compressive pressure applied across the paper web. The finished sheet product is collected on a reel 22. In practice, the portion of the papermaking process near the headbox is referred to as the "wet end", while the portion of the process near the takeup reel is referred to as the "dry end". The wet end is essentially the water removal stage which includes the water removal elements such as table rolls, foils, vacuum foils, and suction boxes while the dry end is essentially the drying stage which includes steam heated dryers and hot air. In accordance with one preferred embodiment, sensor imbedded rollers can be placed in locations within the sheet making machine including roller locations 14, 15, and 22. It should be understood that the roller can also be placed generally anywhere along the line in locations which do not interfere with the sheetmaking process. In another embodiment of the present invention sensor imbedded rollers can be used to direct in-process paper material through the sheetmaking machine. In still another embodiment, in-process paper material is wrapped around sensor imbedded rollers such that the sensors remain in contact with the material to provide prolonged measurement times.

In the case in which the roller resides beneath web 15 at the water removal stage of the sheetmaking machine the materials being measured is the wet stock and the measurements being made are conductivity measurements. As the roller turns, the imbedded sensor array comes in contact with the wetstock on the web. In the case in which the roller is positioned at the drying stage of the machine, the material being measured is a dryer form and the measurements being taken are dielectric constant measurements.

When in contact with the material, the sensor provides a read out giving an instantaneous measurement. In one embodiment, the roller is driven at the same speed as web 13 in the water removal stage such that the point of contact of the sensor and the web does not move thereby eliminating sliding friction, wear on the sensor and residue build-up on the sensor.

Figure 12:
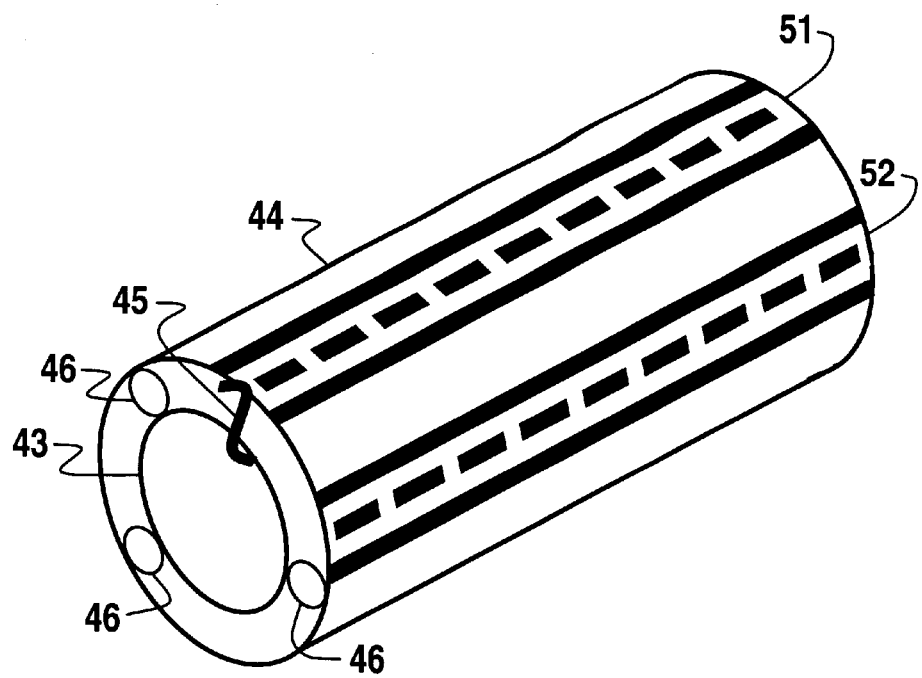
FIG. 12 shows one embodiment of a sensor imbedded roller including a rotatable shell and a stationary inner core portion.

FIG. 12 shows one embodiment of a sensor imbedded roller including a stationary center core portion 43, a rotatable shell 44, a sliding contact assembly 45, and two sensors S1 and S2. Bearings 46 allow for the rotation of the shell 44 about the core 43 although other rotating means can be substituted. Two cross-directional (CD) sensor arrays SI and S2 are imbedded around the circumference of the roll so as to provide two measurements as the roll rotates and each of the arrays come in contact with the web. In another preferred embodiment, four equidistant CD arrays are imbedded in the roll such that four measurements are provided for each revolution of the roll. It should be understood that any number of array can be imbedded. The array electrodes are imbedded on the outer surface of the rotatable shell and are connected to corresponding interior electrodes through the rotating shell. Wires for coupling the remainder of the measurement apparatus to the imbedded sensors are connected to the stationary core. For instance, referring to FIG. 1, wires for connecting Zfixed, Detector 26, and ground to array 24 connect to stationary core 43. The stationary core includes a sliding contact assembly coupled to the wires which makes electrical contact with each imbedded sensor as its corresponding inner contacts passes over the sliding contact assembly. Each sensor in the shell uses the same sliding contact assembly such that only one is in contact with it at a time. It should be noted that the sensor array shown in FIG. 12 corresponds to the array shown in FIG. 1. However, it should be understood that other sensor array embodiments may be substituted.

In another embodiment, the sensor imbedded roller includes processing circuitry imbedded in the center of the roller for processing the detected voltage changes from the imbedded sensor and to output a serialized signal corresponding to the detected voltages on a serial bus from the roller. This embodiment minimizes the number of wire connections from the roller.

Figure 13:
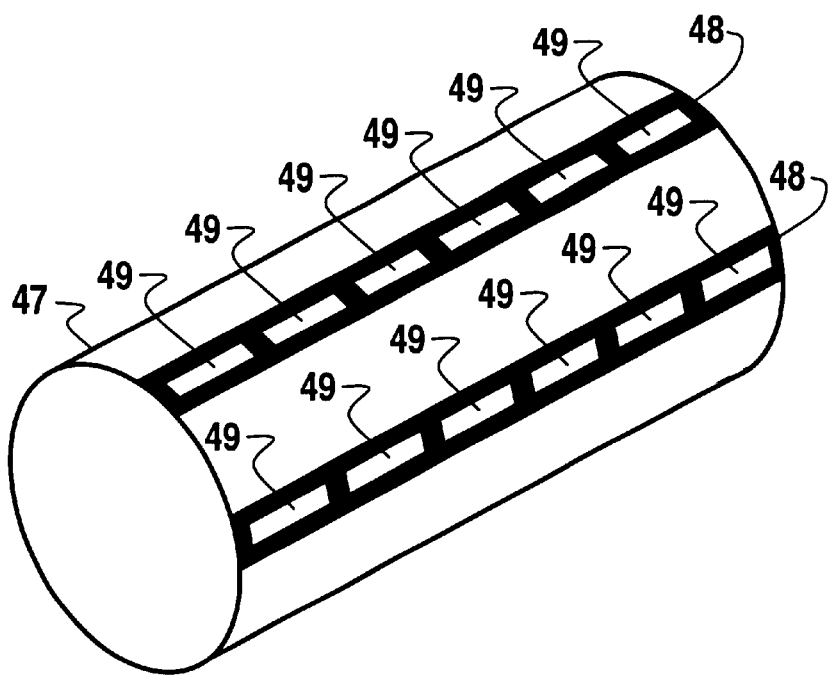
FIG. 13 shows another embodiment of a sensor imbedded roller having dielectric and steel imbedded into a steel roller to form the electrode configuration.

In another embodiment, the sensor imbedded roller is implemented as a metal roller (or a roller having a metal outer surface) having insulating material layers and metal layers imbedded into the outer surface of the shell so as to form the desired electrode configuration. In a preferred embodiment, shown in FIG. 13, the sensor imbedded roller is implemented with a steel outer surface 47. the sensor array corresponds to the array shown in FIG. I having a segmented center elongated electrode and two grounded side electrodes. To form this array in the outer surface 47, a layer of dielectric material 48 is imbedded into surface 47 and steel segments 49 are embedded into dielectric layer 48 such that the segments 49 are electrically insulated from surface 47 so as to form the center segmented electrodes. The outer surface 47 is grounded and effectively functions as the two elongated grounded electrodes 24A and 24B shown in FIG. 1 while the imbedded steel segments 49 effectively function as the center segments 24D(1) . . . 24D(n) shown in FIG. 1.

It should be understood that other array configurations can be implemented in a similar manner by imbedding insulating and metal layers into a metal outer surface or metal roller.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. An apparatus for use in the wet end of a sheetmaking machine including a moving conveyor for the moving and the drainage of a wetstock material that comprises an aqueous fibrous mixture, said apparatus comprising:

a rotatable roller having an outer surface of grounded metal in close proximity to a lower surface said wetstock material on said conveyor wherein the rotatable roller supports the wetstock material;

at least one sensor comprising an electrode configuration that is imbedded within said outer surface for detecting changes in conductivity of said wetstock material, said sensor having a variable resistive impedance such that changes in said conductivity causes changes in resistive impedance of said sensor wherein said electrode comprises a metal layer that is imbedded in said outer surface and a dielectric layer that is imbedded in said outer surface and a single segmented electrode imbedded into said dielectric layer so as to be insulated from said outer surface;

wherein when said roller rotates, said at least one sensor comes essentially in contact with said lower surface of said wetstock material causing said sensor to detect said changes in said conductivity that is proportional to changes in the weight of the wetstock material over said sensor.

2. The apparatus as described in claim 1 wherein said rotatable roller in said apparatus also functions as a roller in a sheetmaking system.

3. The apparatus as described in claim 1 wherein said rotatable roller has an inner region that includes means for processing measured values associated with said changes in resistive impedance received from said sensor and generating data associated with said conductivity.

4. The apparatus as described in claim 3 wherein said processing means serializes said data so as to provide serialized data from said roller.

5. The apparatus as described in claim 1 wherein said roller includes:
   a rotatable outer shell including said outer surface and having an inner surface, said inner surface providing electrical connection to said sensor;
   a stationary inner roller disposed within said shell and having an electrical contact assembly;
   wherein when said outer shell rotates and said at least one sensor comes essentially in contact with said material, said contact assembly makes electrical contact with said electrical connection to said sensor.

6. The apparatus as described in claim 1 wherein said roller is cylindrical.

7. A measurement apparatus for detecting properties of wetstock material that comprises an aqueous fibrous mixture in the wet end of a sheetmaking machine including a moving conveyor for the moving and the drainage of a wetstock material, said apparatus comprising:
   a fixed impedance portion;
   a sensor coupled to said fixed impedance portion between a signal source and a reference potential, said sensor having a variable resistive impedance such that changes in conductivity of said wetstock material causes changes in resistive impedance of said sensor, said sensor including:
      a rotatable roller having an outer surface wherein the rotatable roller supports the wetstock material; and
      at least one means for detecting said changes in conductivity of said wetstock material by sensing said changes in resistive impedance, said detecting means comprises an electrode configuration that is imbedded within said outer surface of said rotatable roller and in close proximity a lower surface of to said wetstock material on said conveyor wherein said electrode configuration includes (i) a first elongated electrode coupled to said reference potential and a segmented elongated electrode coupled to said fixed impedance portion and (ii) a second elongated electrode couples to said reference potential;
      wherein when said roller rotates, said detecting means comes essentially in contact with said lower surface of said wetstock material causing said detecting means to detect said changes in said conductivity that is proportional to changes in the weight of the wetstock material over said detecting means.

8. The apparatus as described in claim 7 wherein said segmented electrode is spaced-apart and centered between said first and second electrodes.

9. The apparatus as described in claim 7 wherein said rotatable roller in said apparatus also functions as a roller in a sheetmaking system.

10. The apparatus as described in claim 7 wherein said outer surface is grounded metal and said electrode configuration comprises a dielectric layer imbedded in said outer surface and a single segmented electrode imbedded in said dielectric layer so as to be insulated from said outer surface, said single segmented electrode being coupled to said fixed impedance portion.

11. The apparatus as described in claim 7 wherein said roller includes:
   a rotatable outer shell including said outer surface and having an inner surface, said inner surface providing electrical connection to said detection means;
   a stationary inner roller disposed within said shell and having an electrical contact assembly, said electrical contact assembly for electrically coupling with other elements of said measurement apparatus that are not included within said roller;
   wherein when said outer shell rotates and said at least one sensor comes essentially in contact with said wetstock material, said contact assembly makes electrical contact with said electrical connection to said sensor.

12. The apparatus as described in claim 7 wherein said apparatus further comprises a means for correlating said changes in said conductivity to fluctuations in physical characteristics of said wetstock material including material weight, chemical composition, and temperature.

13. A system for producing a paper product from a wetstock material that comprises an aqueous fibrous mixture comprising:
   a headbox for dispensing said stock material;
   a water removal stage for receiving said dispensed stock material having at least one webbed conveyor belt, said at least one webbed conveyor belt having a first surface on which said stock material is dispensed and a second surface wherein said water is removed, wherein water is removed from said dispensed material through said belt to produce a web of material;
   a drying stage for drying said web of material to form said paper product;
   a measurement apparatus for detecting changes in conductivity of said wetstock material which includes a fixed impedance portion and sensor coupled to said fixed impedance portion between a signal source and a reference potential, said sensor having a variable impedance such that changes in conductivity of said wetstock material causes changes in impedance of said sensor, said sensor including:
      at least one rotatable roller having an outer surface wherein the rotatable roller supports the wetstock material; and
      at least one means for detecting said changes in conductivity of said wetstock material by sensing said changes in impedance, said detecting means comprising an electrode configuration that is imbedded within said outer surface of said at least one roller wherein said electrode configuration includes (i) a first elongated electrode coupled to said reference potential and a segmented elongated electrode coupled to said fixed impedance portion and (ii) a second elongated electrode couples to said reference potential;
      wherein when said roller rotates, said detecting means comes essentially in close proximity to a lower surface of said wetstock material, causing said detecting means to detect said changes in conductivity that is proportional to changes in the weight of the wetstock material over said detection means.

14. The system as described in claim 13 wherein said system includes at least one sensor in said water removal stage.

15. The system as described in claim 14 wherein said at least one roller is positioned beneath said webbed conveyor belt.

16. The system as described in claim 14 wherein said at least one roller is part of a means for driving said webbed conveyor belt.

17. The system as described in claim 13 wherein said properties include dielectric constant, conductivity, and proximity of said material.

18. The system as described in claim 13 wherein said apparatus further comprises a means for correlating said changes in said properties to fluctuations in physical characteristics of said material including material weight, chemical composition, and temperature.

19. The system as described in claim 13 wherein said at least one roller directs said web of material's movement through said system.

* * * * *